(12) United States Patent
Maruyama

(10) Patent No.: US 10,491,791 B2
(45) Date of Patent: Nov. 26, 2019

(54) IMAGING APPARATUS AND IMAGE SENSOR

(71) Applicant: SONY CORPORATION, Tokyo (JP)

(72) Inventor: Shunsuke Maruyama, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 306 days.

(21) Appl. No.: 15/328,755

(22) PCT Filed: Jun. 19, 2015

(86) PCT No.: PCT/JP2015/067730
§ 371 (c)(1),
(2) Date: Jan. 24, 2017

(87) PCT Pub. No.: WO2016/021312
PCT Pub. Date: Feb. 11, 2016

(65) Prior Publication Data
US 2017/0230557 A1    Aug. 10, 2017

(30) Foreign Application Priority Data
Aug. 8, 2014  (JP) ................................. 2014-163066

(51) Int. Cl.
*H04N 5/225* (2006.01)
*G01N 21/47* (2006.01)
(Continued)

(52) U.S. Cl.
CPC ........... *H04N 5/2258* (2013.01); *G01N 21/47* (2013.01); *G02B 3/0081* (2013.01); *G02B 27/48* (2013.01);
(Continued)

(58) Field of Classification Search
CPC ............ G01N 21/47; G01N 2021/479; H04N 5/2256; H04N 5/2258; H04N 5/332;
(Continued)

(56) References Cited

U.S. PATENT DOCUMENTS

2010/0157117 A1* 6/2010 Wang ................ H01L 27/14621
348/276
2010/0226543 A1   9/2010 Zalevsky
(Continued)

FOREIGN PATENT DOCUMENTS

JP    2008-227250 A    9/2008
JP    2013-003482 A    1/2013
(Continued)

*Primary Examiner* — John R Schnurr
(74) *Attorney, Agent, or Firm* — Chip Law Group

(57) ABSTRACT

To increase the space efficiency of an imaging apparatus which deals with a speckle pattern. An imaging apparatus includes a first image sensor and a second image sensor. The first image sensor images light entering the first image sensor from an object through an optical system to generate image data of the object. The second image sensor images a speckle pattern formed by scattering of light striking the object to generate image data of the speckle pattern, the speckle pattern entering the second image sensor through the optical system. In the imaging apparatus, the first image sensor and the second image sensor are placed side by side in an optical axis direction of the optical system.

14 Claims, 7 Drawing Sheets

(51) Int. Cl.
*G03B 15/00* (2006.01)
*G02B 3/00* (2006.01)
*H01L 27/146* (2006.01)
*H04N 5/33* (2006.01)
*G03B 15/05* (2006.01)
*G02B 27/48* (2006.01)

(52) U.S. Cl.
CPC ............. *G03B 15/00* (2013.01); *G03B 15/05* (2013.01); *H01L 27/1464* (2013.01); *H01L 27/14627* (2013.01); *H01L 27/14636* (2013.01); *H01L 27/14645* (2013.01); *H01L 27/14649* (2013.01); *H04N 5/2256* (2013.01); *H04N 5/332* (2013.01); *G01N 2021/479* (2013.01); *G03B 2215/0567* (2013.01)

(58) Field of Classification Search
CPC ......... H01L 27/14649; H01L 27/14645; H01L 27/14636; H01L 27/14627; H01L 27/1464; G02B 3/0081; G02B 27/48; G03B 15/05; G03B 15/00; G03B 2215/0567

See application file for complete search history.

(56) References Cited

U.S. PATENT DOCUMENTS

| | | | |
|---|---|---|---|
| 2013/0076910 A1* | 3/2013 | Scott | H04N 5/332 348/164 |
| 2014/0194748 A1* | 7/2014 | Yamamoto | A61B 5/0059 600/473 |
| 2015/0249105 A1* | 9/2015 | Skeete | H01L 27/14636 348/374 |
| 2018/0124327 A1* | 5/2018 | Alasirnio | G03B 37/04 |

FOREIGN PATENT DOCUMENTS

| | | |
|---|---|---|
| JP | 2013-123215 A | 6/2013 |
| WO | 2013/027340 A1 | 2/2013 |

* cited by examiner

EXAMPLE IN WHICH SPACER IS PROVIDED
BETWEEN OBJECT IMAGE SENSOR AND SPECKLE IMAGE SENSOR

EXAMPLE IN WHICH OPTICAL SYSTEM IS MOVABLE

EXAMPLE IN WHICH SPECKLE PIXEL FDs
AND OBJECT PIXEL FDs ARE PROVIDED ON SINGLE SUBSTRATE

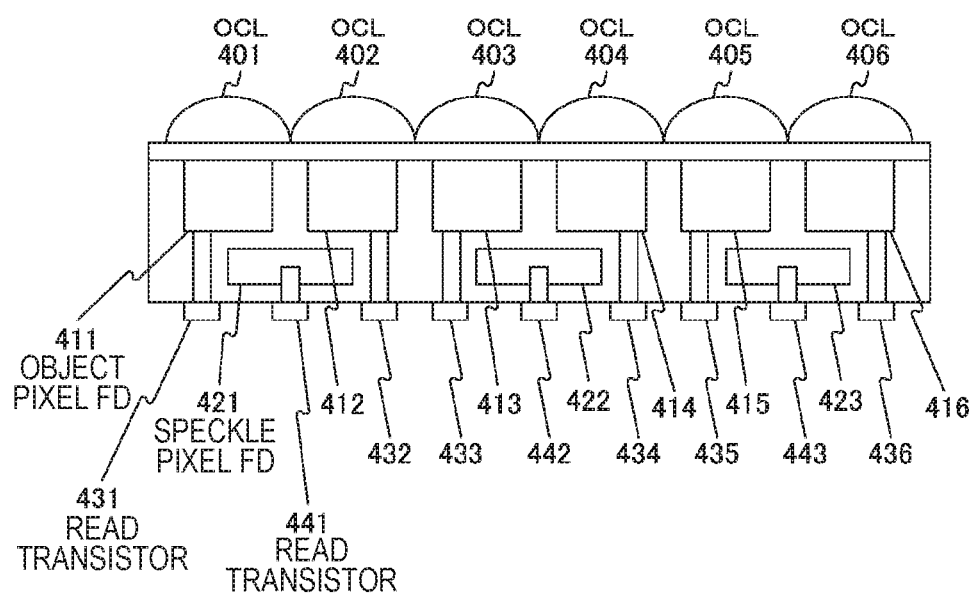

IMAGING APPARATUS AND IMAGE SENSOR

CROSS REFERENCE TO RELATED APPLICATIONS

This application is a U.S. National Phase of International Patent Application No. PCT/JP2015/067730 filed on Jun. 19, 2015, which claims priority benefit of Japanese Patent Application No. JP 2014-163066 filed in the Japan Patent Office on Aug. 8, 2014. Each of the above-referenced applications is hereby incorporated herein by reference in its entirety.

TECHNICAL FIELD

The present technology relates to imaging apparatuses. More particularly, the present technology relates to an imaging apparatus and image sensor which deal with a speckle pattern.

BACKGROUND ART

Conventional techniques of performing various kinds of analysis by utilizing scattering of light striking an object have been proposed. For example, a technique of applying in-phase light (highly coherent light (e.g., laser light)) to a rough surface, and acquiring a grainy pattern (speckle pattern) formed by the scattered light, to perform various kinds of analysis, has been proposed (e.g., Patent Literature 1). For example, by acquiring a speckle pattern and then analyzing an oscillation in the speckle pattern, sound data generated from the rough surface can be acquired.

CITATION LIST

Patent Literature

Patent Literature 1: US 2010/0226543A

DISCLOSURE OF INVENTION

Technical Problem

According to the above conventional technology, various kinds of analysis can be performed on the basis of a speckle pattern.

Here, a speckle pattern is formed in front of an object (closer to an imaging apparatus), and therefore, they have different focal point positions. Therefore, in order to simultaneously acquire an image of an object and an image of a speckle pattern (speckle image), it is necessary for an imaging apparatus to include optical systems for providing different focal point positions.

For example, it is contemplated that two optical systems and two image sensors are provided, and light is brought by the two optical systems to different focal point positions and then captured by two image sensors. Also, it is contemplated that, for example, an optical system, a half mirror, and two image sensors are provided, light collected by the optical system is brought by the half mirror to different focal point positions and then captured by the two image sensors.

However, for mobile imaging apparatuses and the like, there is only limited space for placing an optical system and an image sensor, and therefore, it is important to increase space efficiency.

With the above in mind, the present technology has been made. It is an object of the present technology to increase the space efficiency of an imaging apparatus which deals with a speckle pattern.

Solution to Problem

The present technology has been made to solve the above problem. A first aspect of the present technology is an imaging apparatus including: a first image sensor configured to image light entering the first image sensor from an object through an optical system to generate image data of the object; and a second image sensor configured to image a speckle pattern formed by scattering of light striking the object to generate image data of the speckle pattern, the speckle pattern entering the second image sensor through the optical system. The first image sensor and the second image sensor are placed side by side in an optical axis direction of the optical system. As a result, achieved is the effect of generating image data of an object using a first image sensor, and generating image data of a speckle pattern using a second image sensor, the first and second image sensors being placed side by side in an optical axis direction of an optical system.

According to the first aspect, the second image sensor may be placed on a side opposite to the object with the first image sensor in between in the optical axis direction of the optical system. As a result, achieved is the effect of placing and using a second image sensor on a side opposite to an object with a first image sensor in between in an optical axis direction of an optical system.

According to the first aspect, the first image sensor may transmit light in a wavelength region to be received by the second image sensor, among the light entering the first image sensor through the optical system. As a result, achieved is the effect of causing a first image sensor to transmit light in a wavelength region to be received by a second image sensor, of light entering the first image sensor through an optical system.

According to the first aspect, a spacer may be provided between the first image sensor and the second image sensor. As a result, achieved is the effect of providing and using a spacer between a first image sensor and a second image sensor.

According to the first aspect, the spacer may transmit light in a wavelength region to be received by the second image sensor. As a result, achieved is the effect of causing a spacer to transmit light in a wavelength region to be received by a second image sensor.

According to the first aspect, the spacer may have optical characteristics for cutting off visible light. As a result, achieved is the effect of using a spacer having optical characteristics for cutting off visible light.

According to the first aspect, at least one of the first image sensor and the second image sensor may be movable in the optical axis direction of the optical system. As a result, achieved is the effect of causing at least one of a first image sensor and a second image sensor to be movable in an optical axis direction of an optical system.

According to the first aspect, the first image sensor and the second image sensor may be electrically coupled together using a bump. As a result, achieved is the effect of using a first image sensor and a second image sensor electrically coupled together using a bump.

According to the first aspect, another optical system may be provided between the first image sensor and the second image sensor. As a result, achieved is the effect of using another optical system provided between a first image sensor and a second image sensor.

According to the first aspect, the other optical system may be movable in the optical axis direction of the optical system. As a result, achieved is the effect of causing another optical system to be movable in an optical axis direction of an optical system.

According to the first aspect, the other optical system may be a lens capable of changing at least one of a shape and a refractive index in accordance with an external signal. As a result, achieved is the effect of using a lens capable of changing at least one of a shape and a refractive index in accordance with an external signal.

According to the first aspect, the first image sensor may receive visible light to generate the image data of the object, and the second image sensor may receive infrared light to generate the image data of the speckle pattern. As a result, achieved is the effect of causing a first image sensor to receive visible light to generate image data of an object, and causing a second image sensor to receive infrared light to generate image data of a speckle pattern.

According to the first aspect, a cell size of the second image sensor may be greater than a cell size of the first image sensor. As a result, achieved is the effect of causing a cell size of a second image sensor to be greater than a cell size of a first image sensor, and generating each piece of image data.

According to the first aspect, a frame rate of the image data generated by the second image sensor may be higher than a frame rate of the image data generated by the first image sensor. As a result, achieved is the effect of causing a frame rate of image data generated by a second image sensor to be higher than a frame rate of image data generated by a first image sensor.

A second aspect of the present technology is an image sensor in which a first light reception unit configured to receive light entering the first light reception unit from an object through an optical system to generate image data of the object, and a second light reception unit configured to receive a speckle pattern of light formed by scattering of light striking the object to generate image data of the speckle pattern, the speckle pattern of light entering the second light reception unit through the optical system, are provided on a single substrate. As a result, achieved is the effect of using an image sensor in which a first light reception unit and a second light reception unit are provided on a single substrate.

According to the second aspect, the second light reception unit may be placed on a side opposite to the object with the first light reception unit in between in an optical axis direction of the optical system. As a result, achieved is the effect of placing and using a second light reception unit on a side opposite to an object with reference to a first light reception unit in an optical axis direction of an optical system.

According to the second aspect, the second light reception unit may be longer than the first light reception unit in the optical axis direction of the optical system. As a result, achieved is the effect of using a second light reception unit longer than a first light reception unit in an optical axis direction of an optical system.

According to the second aspect, a cell size of the second light reception unit may be greater than a cell size of the first light reception unit. As a result, achieved is the effect of causing a cell size of a second light reception unit to be greater than a cell size of a first light reception unit, and generating each piece of image data.

According to the second aspect, a frame rate of the image data generated by the second light reception unit may be higher than a frame rate of the image data generated by the first light reception unit. As a result, achieved is the effect of causing a frame rate of image data generated by a second light reception unit to be higher than a frame rate of image data generated by a first light reception unit.

According to the second aspect, an on-chip lens provided in the first light reception unit and an on-chip lens provided in the second light reception unit may have different shapes. As a result, achieved is the effect of using an on-chip lens provided in the first light reception unit and an on-chip lens provided in the second light reception unit, the on-chip lenses having different shapes.

Advantageous Effects of Invention

According to the present technology, the excellent effect of increasing the space efficiency of an imaging apparatus which deals with a speckle pattern can be exhibited. Note that the effects described here are not necessarily limited, and any effect that is desired to be described in the present disclosure may be exhibited.

BRIEF DESCRIPTION OF DRAWINGS

FIG. 7 is a cross-sectional view showing an internal configuration example of an image sensor in a fifth embodiment of the present technology.

MODE(S) FOR CARRYING OUT THE INVENTION

Modes for carrying out the present technology (hereinafter referred to as "embodiments") will now be described. The description will be provided in the following order.
1. First embodiment (an example in which a speckle image sensor and an object image sensor are fixed and placed side by side in the optical axis direction of an optical system)
2. Second embodiment (an example in which at least one of a speckle image sensor and an object image sensor is movable in the optical axis direction of an optical system)
3. Third embodiment (an example in which an additional optical system which is movable is provided between a speckle image sensor and an object image sensor)

4. Fourth embodiment (an example of an image sensor in which speckle pixel photodiodes (PDs) and object pixel PDs are provided on a single substrate)

5. Fifth embodiment (a variation of an image sensor in which speckle pixel PDs and object pixel PDs are provided on a single substrate)

1. First Embodiment

Example of Use of Imaging Apparatus

Figure 1:
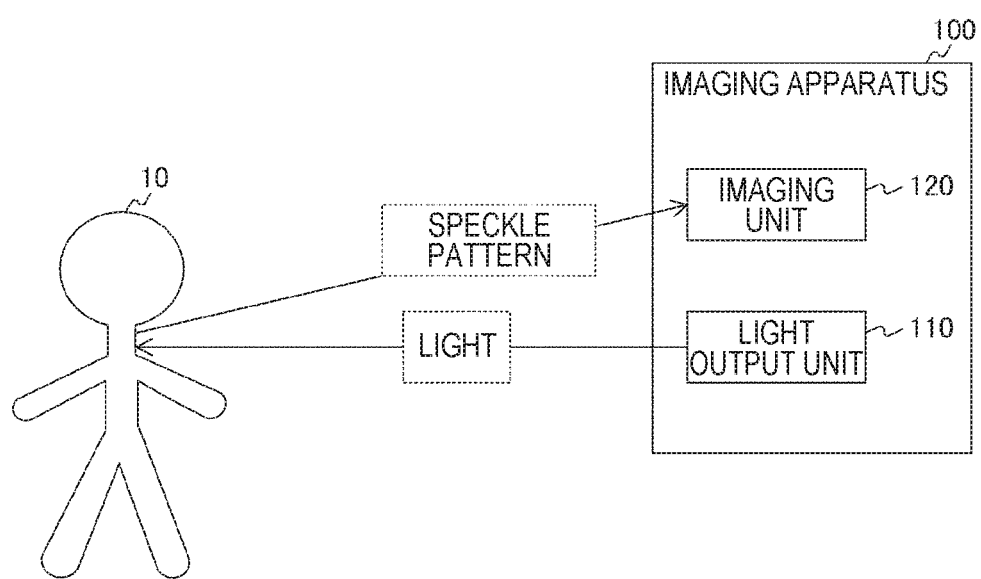
FIG. 1 is a diagram showing an example of use of an imaging apparatus 100 in a first embodiment of the present technology.

FIG. 1 is a diagram showing an example of use of an imaging apparatus 100 in a first embodiment of the present technology.

The imaging apparatus 100 outputs highly coherent light (e.g., laser light) from a light output unit 110 to a person 10, and acquires a speckle pattern formed by the scattered light using an imaging unit 120. Thereafter, the imaging apparatus 100 can acquire various kinds of information (e.g., sound data, distance information) on the basis of an oscillation in the acquired speckle pattern.

Here, as the highly coherent light, highly directional light can be used, for example. Therefore, a specific sound emitted by an object relatively far away from the imaging apparatus 100 can be acquired. For example, even when there is a relatively large distance between the imaging apparatus 100 and the person 10, a sound (voice) uttered by the person 10 can be acquired by outputting highly directional laser light from the light output unit 110 toward the throat of the person 10.

Thus, sound data can be obtained on the basis of an oscillation in a speckle pattern formed by scattered beams of highly coherent light, such as laser light or the like, which is applied to a rough surface. Such use of highly directional light allows for acquisition of sound data of a specific object of interest remotely located.

Configuration Example of Imaging Apparatus

Figure 2:
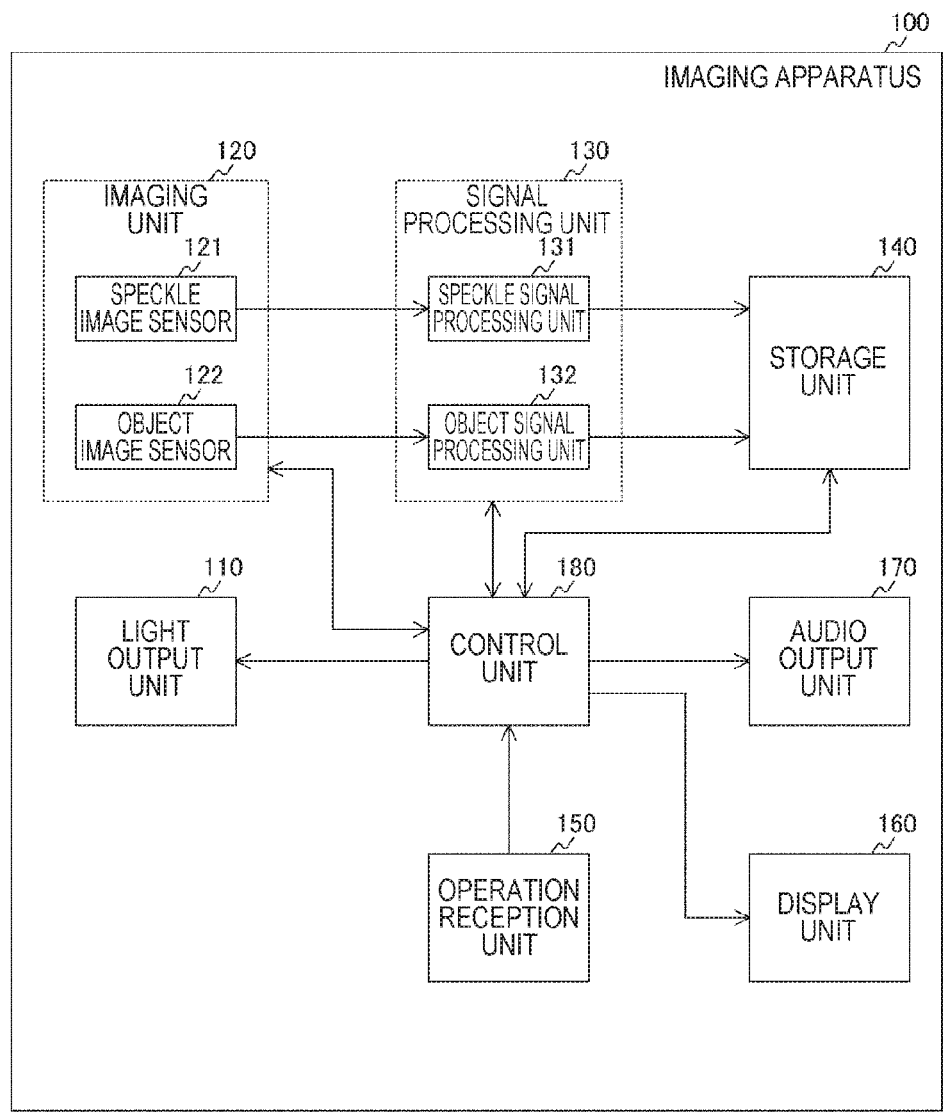
FIG. 2 is a block diagram showing a functional configuration example of the imaging apparatus 100 in the first embodiment of the present technology.

FIG. 2 is a block diagram showing a functional configuration example of the imaging apparatus 100 in the first embodiment of the present technology.

The imaging apparatus 100 includes the light output unit 110, the imaging unit 120, a signal processing unit 130, a storage unit 140, an operation reception unit 150, a display unit 160, an audio output unit 170, and a control unit 180.

The light output unit 110 outputs highly coherent light (e.g., laser light) under the control of the control unit 180.

Figure 3:
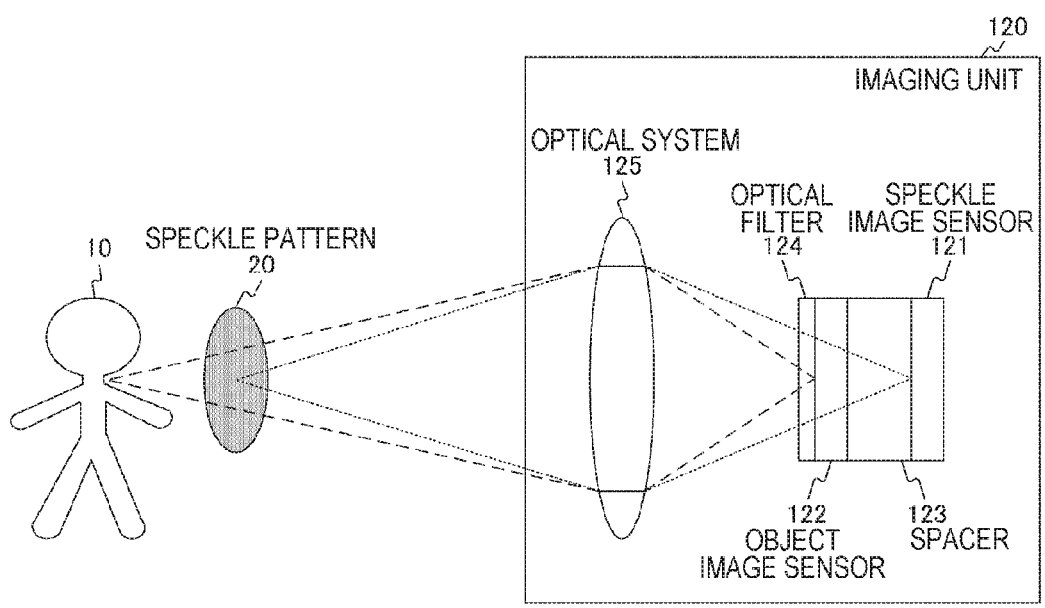
FIG. 3 is a diagram showing an internal configuration example of an imaging unit 120 in the first embodiment of the present technology.

The imaging unit 120 images an object of interest to generate image data, and outputs the generated image data to the signal processing unit 130, under the control of the control unit 180. Specifically, the imaging unit 120 includes the speckle image sensor 121 and the object image sensor 122. Note that although the imaging unit 120 includes a optical system 125 as shown in FIG. 3, the optical system 125 is not shown in FIG. 2. Also, the speckle image sensor 121 is an example of a second image sensor described in the accompanying claims. Also, the object image sensor 122 is an example of a first image sensor described in the accompanying claims.

Here, the size of image data generated by the speckle image sensor 121 can be smaller than the size of image data generated by the object image sensor 122. For example, the size of image data generated by the object image sensor 122 can be of full high definition (HD) (1920×1080 pixels). In this case, for example, the size of image data generated by the speckle image sensor 121 can be reduced to Video Graphics Array (VGA) (640×480 pixels) or approximately VGA.

Also, the speckle image sensor 121 and the object image sensor 122 can have different cell sizes. For example, the cell size of the object image sensor 122 can be smaller than the cell size of the speckle image sensor 121.

Also, because the image data generated by the speckle image sensor 121 is used for acquisition of sound data, it is necessary for the image data generated by the speckle image sensor 121 to have a higher frame rate than that of the image data generated by the object image sensor 122. For example, the image data generated by the object image sensor 122 may have a frame rate of 30 to 60 frames per second (fps). In this case, for example, the image data generated by the speckle image sensor 121 may have a frame rate of about several thousands to several tens of thousands of fps.

The signal processing unit 130 performs various signal processes on the image data generated by the imaging unit 120, and records into the storage unit 140 the image data which has been subjected to the signal processes, under the control of the control unit 180.

Specifically, the signal processing unit 130 includes a speckle signal processing unit 131 and an object signal processing unit 132. The object signal processing unit 132 performs various signal processes on the image data (e.g., moving image data) generated by the object image sensor 122. Thereafter, the object signal processing unit 132 outputs to the control unit 180 the image data which has been subjected to the signal processes, and records that image data as an image content (e.g., a moving image file) into the storage unit 140.

The speckle signal processing unit 131 performs various signal processes on the image data (image data of a speckle pattern) generated by the speckle image sensor 121. Thereafter, the speckle signal processing unit 131 outputs to the control unit 180 the image data which has been subjected to the signal processes, and records into the storage unit 140 that image data (e.g., a moving image file) as accompanying information, in association with the image content that is simultaneously generated.

The storage unit 140 is a recording medium into which each item of information is stored under the control of the control unit 180. For example, the storage unit 140 stores image data which has been generated by the object image sensor 122 and then subjected to signal processes by the object signal processing unit 132, as an image content (e.g., a moving image file). Also, for example, the storage unit 140 stores image data (image data of a speckle pattern) which has been generated by the speckle image sensor 121 and then subjected to signal processes by the speckle signal processing unit 131, as accompanying information, in association with the image content.

The operation reception unit 150 is an operation reception unit which receives an operation performed by the user, and outputs control information (operation information) corresponding to the received operation to the control unit 180. Note that the operation reception unit 150 is implemented by, for example, an operation member, such as a button, switch, or the like.

The display unit 160 displays various images under the control of the control unit 180. The display unit 160 is implemented by, for example, a display panel, such as a liquid crystal display (LCD), electroluminescence (EL) panel, or the like.

Note that at least a portion of the operation reception unit 150 and the display unit 160 may be integrally configured.

For example, the operation reception unit 150 and the display unit 160 can be configured as a capacitive (capacitance type) touchscreen which detects touch or proximity of a conductive object (e.g., a finger of a person) on the basis of a change in capacitance.

The audio output unit 170 outputs sound data under the control of the control unit 180. The audio output unit 170 is implemented by, for example, a loudspeaker.

The control unit 180 controls each unit in the imaging apparatus 100 according to a control program. For example, the control unit 180 controls an imaging operation so that pieces of image data generated by the imaging unit 120 are sequentially recorded into the storage unit 140. Also, for example, the control unit 180 performs a playback process on an image content stored in the storage unit 140.

Also, for example, the control unit 180 generates and acquires sound data related to an object which is within an imaging range on the basis of image data of a speckle pattern.

Configuration Example of Imaging Unit

FIG. 3 is a diagram showing an internal configuration example of the imaging unit 120 in the first embodiment of the present technology. FIG. 3 shows a configuration example in a case where a spacer 123 is provided between the speckle image sensor 121 and the object image sensor 122.

The imaging unit 120 includes the speckle image sensor 121, the object image sensor 122, the spacer 123, an optical filter 124, and an optical system 125.

The speckle image sensor 121 is an image sensor which receives a portion of light entering through the optical system 125, and generates image data of a speckle pattern 20. The object image sensor 122 is an image sensor which receives a portion of light entering through the optical system 125, and generates image data of an object. In other words, the object image sensor 122 is different from the speckle image sensor 121 in that the object image sensor 122 generates image data to be recorded, while the speckle image sensor 121 generates image data of the speckle pattern 20 of scattered beams of light output from the light output unit 110. Note that, as these image sensors, a charge coupled device (CCD) image sensor or a complementary metal oxide semiconductor (CMOS) image sensor can be used, for example.

Here, the object image sensor 122 transmits a portion of light collected by the optical system 125 so that the portion of the light is received by the speckle image sensor 121. Specifically, the object image sensor 122 transmits a wavelength region of light which is to be received by the speckle image sensor 121, of light collected by the optical system 125.

For example, as the object image sensor 122, an image sensor capable of receiving visible light (e.g., 700 nm or less, or 750 nm or less) can be used. In this case, for example, as the speckle image sensor 121, an image sensor capable of receiving infrared light (e.g., 700 nm or more, 750 nm or more, or a specific infrared laser wavelength) can be used.

Here, for example, it is assumed that 850-nm laser light is used as light output by the light output unit 110. In this case, an IR cut-off filter having 850-nm band-pass characteristics is preferably provided on the incident light side of the object image sensor 122.

Also, for example, it is assumed that laser light at 1200 nm or more is used as light output by the light output unit 110. In this case, a cut-off filter for blocking about 700 nm or about 750 nm to 1200 nm is preferably provided on the incident light side of the object image sensor 122.

Also, the speckle image sensor 121 can be, for example, an image sensor employing a compound semiconductor other than silicon (Si).

Also, the speckle image sensor 121 and the object image sensor 122 can be electrically coupled together using a bump.

The spacer 123 is a plate-shaped member provided between the speckle image sensor 121 and the object image sensor 122. Also, the spacer 123 is preferably formed of a material which transmits a wavelength region of light which is to be received by the speckle image sensor 121. Also, the spacer 123 is preferably formed of a material having optical characteristics, such as visible light cut-off characteristics or the like.

The optical filter 124 is a filter which removes unnecessary wavelengths. For example, the optical filter 124 can block light in a predetermined wavelength region.

The optical system 125 includes a plurality of lenses (e.g., a zoom lens, a focusing lens) for bringing light from an object into focus.

For example, when laser light is applied to an object having a rough surface (e.g., the skin of a person), a speckle pattern is formed by reflection of the light. Specifically, light beams of the laser light scattered from positions on the surface of the object are superposed together. Thus, the superposition of light beams having different phases forms a speckle pattern.

Also, laser light reflected from an object spreads out more as it goes away from the object. Therefore, it is preferable to acquire a speckle pattern which is formed closer to the imaging apparatus 100 than to the object. For example, when a distance between the imaging apparatus 100 and an object of interest is 5 m, a speckle pattern which is formed at a position which is about 1 m away from the object of interest can be acquired and used.

Thus, the speckle pattern 20 of the object 10 is formed in front of the object 10 (closer to the imaging apparatus 100). Therefore, in order to simultaneously acquire an image of the object 10 and an image of the speckle pattern 20 (speckle image), it is necessary for these images to have different focal point positions. To this end, in the first embodiment of the present technology, the speckle image sensor 121 and the object image sensor 122 are fixed and placed side by side in the optical axis direction of the optical system 125. As a result, the space efficiency of the imaging apparatus 100 which deals with a speckle pattern can be increased.

Also, a speckle pattern is wave-like information, whose motion is recognized as an oscillation, and the oscillation is converted into a signal, which is used. For example, laser reflected from a moving portion of an object (e.g., a portion of the throat when a voice is uttered) moves on a speckle pattern. This movement can be recognized as an oscillation. Also, an acquired speckle pattern can be used for modification of an object, speech analysis, vibration analysis, or the like. For example, when sound data is acquired on the basis of an acquired speckle pattern, sound data can be acquired by a matching process between an oscillation in the acquired speckle pattern and vibration information for identifying sound data.

2. Second Embodiment

In the first embodiment of the present technology, an example has been shown in a speckle image sensor and an object image sensor are fixed and placed side by side in the optical axis direction of an optical system. In a second embodiment of the present technology, at least one of a speckle image sensor and an object image sensor is movable in the optical axis direction of an optical system.

Configuration Example of Imaging Unit

Figure 4:
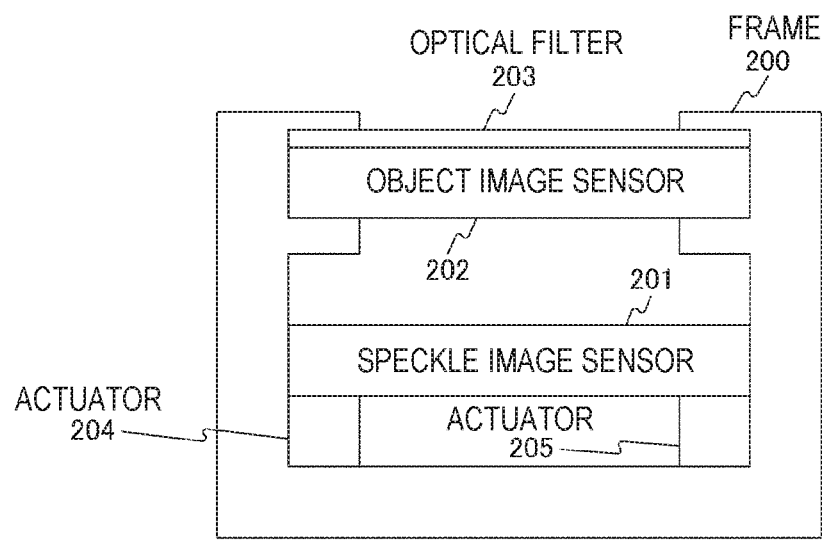
FIG. 4 is a diagram showing an internal configuration example of an imaging unit in a second embodiment of the present technology.

FIG. 4 is a diagram showing an internal configuration example of an imaging unit in the second embodiment of the present technology. In FIG. 4, a configuration example is shown in which a speckle image sensor 201 is movable. Note that, in FIG. 4, it is assumed that the vertical direction is the optical axis direction of the optical system. Also, in FIG. 5 to FIG. 7, it is similarly assumed that the vertical direction is the optical axis direction of an optical system.

The imaging unit shown in FIG. 4 includes a frame 200, the speckle image sensor 201, an object image sensor 202, an optical filter 203, and actuators 204 and 205. Note that the speckle image sensor 201, the object image sensor 202, and the optical filter 203 are similar to those shown in FIG. 3 which have the same names. Therefore, these will not be here described. Also, the imaging unit shown in FIG. 4 is a variation of the imaging unit 120 shown in FIG. 1 to FIG. 3. Therefore, some of the imaging unit 120 and portions related thereto that are similar to those of the first embodiment of the present technology are indicated by the same reference signs as those of the first embodiment of the present technology and will not be fully described.

The frame 200 is a frame for supporting and fixing each unit (the speckle image sensor 201, the object image sensor 202, the optical filter 203, and the actuators 204 and 205).

The actuators 204 and 205 are actuators which move the speckle image sensor 201 forward and backward (upward and downward in FIG. 4) in the optical axis direction (the vertical direction of FIG. 4) of the optical system under the control of the control unit 180 (shown in FIG. 2).

Thus, the speckle image sensor 201 can be moved forward and backward in the optical axis direction of the optical system. As a result, the focal point position of the speckle image sensor 201 can be adjusted, whereby the accuracy of acquisition of image data of a speckle pattern can be further increased.

Note that although, in FIG. 4, an example has been described in which only the speckle image sensor 201 is moved in the optical axis direction of the optical system, the object image sensor 202 may be moved. Also, both the speckle image sensor 201 and the object image sensor 202 may be moved in the optical axis direction of the optical system. In this case, for example, both the speckle image sensor 201 and the object image sensor 202 may each independently be moved in the optical axis direction of the optical system.

As a result, the focal point positions of the speckle image sensor 201 and the object image sensor 202 can be adjusted, whereby the accuracy of acquisition of image data of an object and image data of a speckle pattern can be further increased. Also, the space efficiency of an imaging apparatus which deals with a speckle pattern can be increased.

3. Third Embodiment

In the second embodiment of the present technology, an example has been shown in which at least one of a speckle image sensor and an object image sensor is movable in the optical axis direction of an optical system. In a third embodiment of the present technology, an example is shown in which another optical system which is movable is provided between a speckle image sensor and an object image sensor.

Configuration Example of Imaging Unit

Figure 5:
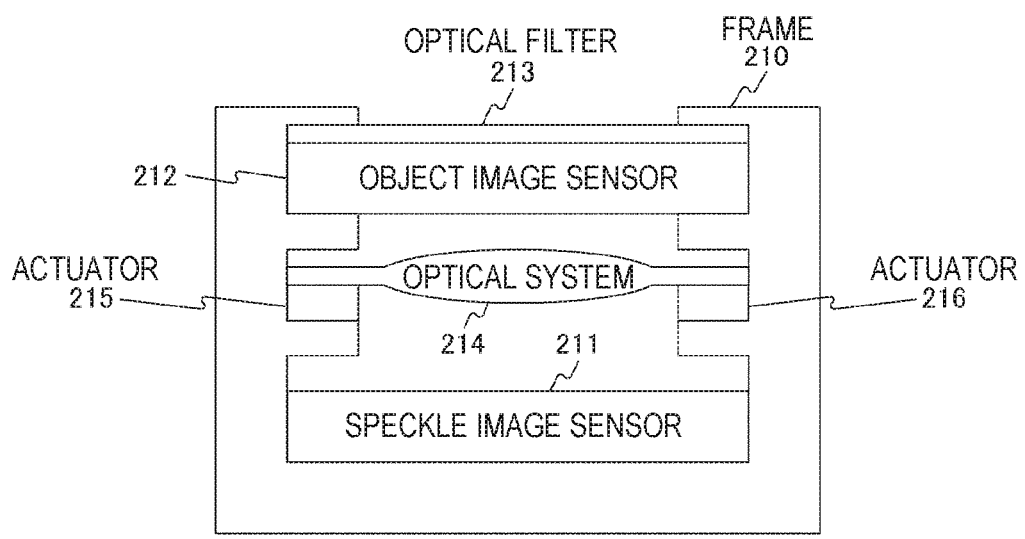
FIG. 5 is a diagram showing an internal configuration example of an imaging unit in a third embodiment of the present technology.

FIG. 5 is a diagram showing an internal configuration example of an imaging unit in the third embodiment of the present technology.

The imaging unit shown in FIG. 5 includes a frame 210, a speckle image sensor 211, an object image sensor 212, an optical filter 213, an optical system 214, and actuators 215 and 216. Note that the frame 200, the speckle image sensor 211, the object image sensor 212, and the optical filter 213 are similar to those shown in FIG. 4 which have the same names. Therefore, these will not be here described.

The optical system 214 includes one or more lenses for bringing light which has transmitted through the object image sensor 212 into focus. Note that the optical system 214 is an example of another optical system described in the accompanying claims.

The actuators 215 and 216 are actuators for moving the optical system 214 forward and backward (upward and downward in FIG. 5) in the optical axis direction (the vertical direction of FIG. 5) of the optical system under the control of the control unit 180 (shown in FIG. 2).

Thus, the optical system 214 can be moved forward and backward in the optical axis direction of the optical system. As a result, the focal point position of the speckle image sensor 211 can be adjusted, whereby the accuracy of acquisition of image data of a speckle pattern can be further increased. Also, the space efficiency of an imaging apparatus which deals with a speckle pattern can be increased.

Note that, in FIG. 5, an example has been described in which a commonly used lens is provided as the optical system 214 and is moved in the optical axis direction of the optical system. Note that a lens whose shape, refractive index, or the like can be changed under external control (e.g., a liquid lens, a liquid crystal lens) may be provided in the optical axis direction of the optical system. In this case, for example, the focal point position of the speckle image sensor 201 can be adjusted by changing the shape, refractive index, or the like of the lens under the control of the control unit 180 (shown in FIG. 2).

4. Fourth Embodiment

In the first to third embodiments of the present technology, examples have been described in which a speckle image sensor and an object image sensor are placed side by side in the optical axis direction of an optical system. In a fourth embodiment of the present technology, shown is an example of an image sensor in which speckle pixel photodiodes (PDs) and object pixel PDs are provided on a single substrate.

Configuration Example of Image Sensor

Figure 6:
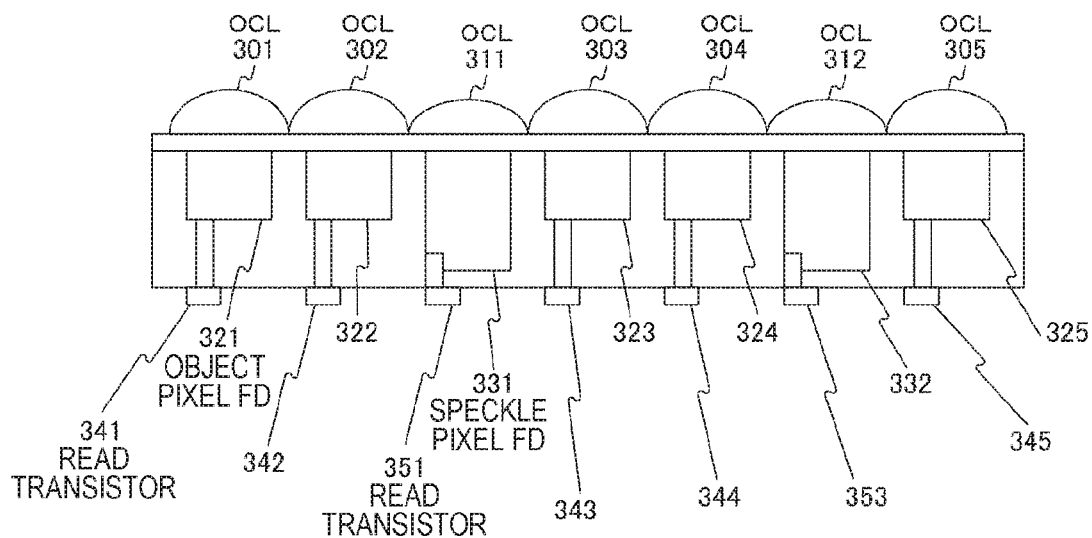
FIG. 6 is a cross-sectional view showing an internal configuration example of an image sensor in a fourth embodiment of the present technology.

FIG. 6 is a cross-sectional view showing an internal configuration example of an image sensor in the fourth embodiment of the present technology.

The image sensor shown in FIG. 6 includes on-chip lenses (OCL) 301 to 305, 311, and 312, object pixel PDs 321 to 325, speckle pixel PDs 331 and 332, and read transistors 341 to 345, 351, and 352.

The OCLs 301 to 305 are micro-lenses for bringing light from an object into focus at the object pixel PDs 321 to 325.

The OCLs 311 and 312 are micro-lenses for bringing light from a speckle pattern into focus at the speckle pixel PDs 331 and 332.

Note that, in FIG. 6, an example is shown in which the on-chip lenses for the object pixel PDs 321 to 325 and the on-chip lenses for the speckle pixel PDs 331 and 332 have different physical structures (e.g., a diameter, curvature).

The object pixel PDs 321 to 325 are light reception elements (photodiodes) for receiving light beams which have been brought into focus by the OCLs 301 to 305. Note that the object pixel PDs 321 to 325 are an example of a first light reception unit described in the accompanying claims.

The speckle pixel PDs 331 and 332 are light reception elements (photodiodes) for receiving light beams which have been brought into focus by the OCLs 311 and 312. Note that speckle pixel PDs 331 and 332 are an example of a second light reception unit described in the accompanying claims.

Also, the speckle pixel PDs 331 and 332 are longer than the object pixel PDs 321 to 325 in the optical axis direction of the optical system (the vertical direction of FIG. 6).

Also, the object pixel PDs 321 to 325 are light reception elements for generating image data to be recorded. Also, the speckle pixel PDs 331 and 332 are light reception elements for generating image data of a speckle pattern of scattered beams of light output by the light output unit 110.

Here, the size of image data generated by the speckle pixel PDs 331 and 332 can be smaller than the size of image data generated by the object pixel PDs 321 to 325. For example, as shown in the first embodiment of the present technology, the size of image data generated by the object pixel PDs 321 to 325 can be of full HD. In this case, for example, the size of image data generated by the speckle pixel PDs 331 and 332 can be reduced to VGA or approximately VGA.

Also, the object pixel PDs 321 to 325 and the speckle pixel PDs 331 and 332 can have different cell sizes. For example, the cell size of the object pixel PDs 321 to 325 can be smaller than the cell size of the speckle pixel PDs 331 and 332.

Also, because the image data generated by the speckle pixel PDs 331 and 332 is used for acquisition of sound data, it is necessary for the image data generated by the speckle pixel PDs 331 and 332 to have a higher frame rate than that of the image data generated by the object pixel PDs 321 to 325. For example, as shown in the first embodiment of the present technology, the image data generated by the object pixel PDs 321 to 325 may have a frame rate of 30 fps to 60 fps. In this case, for example, the image data generated by the speckle pixel PDs 331 and 332 may have a frame rate of about several thousands to several tens of thousands of fps.

The read transistors 341 to 345 are read transistors which are used to read pixel data accumulated in the object pixel PDs 321 to 325 which have received light.

The read transistors 351 and 352 are read transistors which are used to read pixel data accumulated in the speckle pixel PDs 331 and 332 which have received light.

Thus, speckle pixel PDs and object pixel PDs can be provided on a single substrate. As a result, the space efficiency of an imaging apparatus which deals with a speckle pattern can be increased.

5. Fifth Embodiment

In the fourth embodiment of the present technology, an example of an image sensor has been shown in which speckle pixel PDs and object pixel PDs can be provided on a single substrate. In a fifth embodiment of the present technology, a variation of the fourth embodiment of the present technology is shown.

Configuration Example of Image Sensor

FIG. 7 is a cross-sectional view showing an internal configuration example of an image sensor in the fifth embodiment of the present technology.

The image sensor shown in FIG. 7 includes OCLs 401 to 406, object pixel PDs 411 to 416, speckle pixel PDs 421 to 423, and read transistors 431 to 436 and 441 to 443.

Here, the image sensor shown in FIG. 7 is obtained by modifying the image sensor shown in FIG. 6 so that the shape of the speckle pixel PD is changed and the OCL for the speckle pixel PD is removed. Also, except for these differences, the image sensor shown in FIG. 7 is generally similar to the image sensor shown in FIG. 6, and therefore, only the differences will be here described in detail.

Specifically, in the image sensor shown in FIG. 7, the speckle pixel PDs 421 to 423 are placed on the side opposite to an object with the object pixel PDs 411 to 416 in between in the optical axis direction of optical system (the vertical direction of FIG. 7).

Thus, the speckle pixel PDs and the object pixel PDs are provided on a single substrate. As a result, the space efficiency of an imaging apparatus which deals with a speckle pattern can be increased.

Thus, according to the embodiments of the present technology, an optimum structure with increased space efficiency can be implemented for an imaging apparatus and image sensor which acquire image data of an object and image data of a speckle pattern of the object.

Specifically, in the first to third embodiments of the present technology, a speckle image sensor which receives light which transmits an object image sensor is placed behind the object image sensor in the optical axis direction of an optical system. Also, the object image sensor and the speckle image sensor are stacked (placed) with a space being provided therebetween in the optical axis direction of the optical system so that they have different focal point positions.

Also, in the fourth and fifth embodiments of the present technology, object pixel FDs and speckle pixel FDs are provided on the same substrate.

As a result, focus can be put on each of an object and a speckle pattern without using a plurality of optical systems. In other words, image data of a speckle pattern can be acquired using a speckle image sensor (speckle pixel FDs) while an object image sensor (object pixel FDs) is exactly focused on an object, without using a plurality of optical systems.

The above-described embodiments are examples for embodying the present technology, and matters in the embodiments each have a corresponding relationship with disclosure-specific matters in the claims. Likewise, the matters in the embodiments and the disclosure-specific matters in the claims denoted by the same names have a corresponding relationship with each other. However, the present technology is not limited to the embodiments, and various modifications of the embodiments may be embodied in the scope of the present technology without departing from the spirit of the present technology.

In addition, the effects described in the present specification are not limiting but are merely examples, and there may be additional effects.

Additionally, the present technology may also be configured as below.

(1) An imaging apparatus including:
a first image sensor configured to image light entering the first image sensor from an object through an optical system to generate image data of the object; and
a second image sensor configured to image a speckle pattern formed by scattering of light striking the object to generate image data of the speckle pattern, the speckle pattern entering the second image sensor through the optical system,
wherein
the first image sensor and the second image sensor are placed side by side in an optical axis direction of the optical system.

(2) The imaging apparatus according to (1), wherein
the second image sensor is placed on a side opposite to the object with the first image sensor in between in the optical axis direction of the optical system.

(3) The imaging apparatus according to (2), wherein
the first image sensor transmits light in a wavelength region to be received by the second image sensor, among the light entering the first image sensor through the optical system.

(4) The imaging apparatus according to any of (1) to (3), wherein
a spacer is provided between the first image sensor and the second image sensor.

(5) The imaging apparatus according to (4), wherein
the spacer transmits light in a wavelength region to be received by the second image sensor.

(6) The imaging apparatus according to (4) or (5), wherein
the spacer has optical characteristics for cutting off visible light.

(7) The imaging apparatus according to any of (1) to (3), wherein
at least one of the first image sensor and the second image sensor is movable in the optical axis direction of the optical system.

(8) The imaging apparatus according to any of (1) to (7), wherein
the first image sensor and the second image sensor are electrically coupled together using a bump.

(9) The imaging apparatus according to any of (1) to (3), wherein
another optical system is provided between the first image sensor and the second image sensor.

(10) The imaging apparatus according to (9), wherein
the other optical system is movable in the optical axis direction of the optical system.

(11) The imaging apparatus according to (9), wherein
the other optical system is a lens capable of changing at least one of a shape and a refractive index in accordance with an external signal.

(12) The imaging apparatus according to any of (1) to (11), wherein
the first image sensor receives visible light to generate the image data of the object, and
the second image sensor receives infrared light to generate the image data of the speckle pattern.

(13) The imaging apparatus according to any of (1) to (12), wherein
a cell size of the second image sensor is greater than a cell size of the first image sensor.

(14) The imaging apparatus according to any of (1) to (13), wherein a frame rate of the image data generated by the second image sensor is higher than a frame rate of the image data generated by the first image sensor.

(15) An image sensor, wherein
a first light reception unit configured to receive light entering the first light reception unit from an object through an optical system to generate image data of the object, and
a second light reception unit configured to receive a speckle pattern of light formed by scattering of light striking the object to generate image data of the speckle pattern, the speckle pattern of light entering the second light reception unit through the optical system, are provided on a single substrate.

(16) The image sensor according to (15), wherein
the second light reception unit is placed on a side opposite to the object with the first light reception unit in between in an optical axis direction of the optical system.

(17) The image sensor according to (15) or (16), wherein the second light reception unit is longer than the first light reception unit in the optical axis direction of the optical system.

(18) The image sensor according to any of (15) to (17), wherein a cell size of the second light reception unit is greater than a cell size of the first light reception unit.

(19) The image sensor according to any of (15) to (18), wherein a frame rate of the image data generated by the second light reception unit is higher than a frame rate of the image data generated by the first light reception unit.

(20) The image sensor according to any of (15) to (19), wherein an on-chip lens provided in the first light reception unit and an on-chip lens provided in the second light reception unit have different shapes.

REFERENCE SIGNS LIST 100 imaging apparatus
110 light output unit
120 imaging unit
121 speckle image sensor
122 object image sensor
123 spacer
124 optical filter
125 optical system
130 signal processing unit
131 speckle signal processing unit
132 object signal processing unit
140 storage unit
150 sound acquisition unit
160 display unit
170 audio output unit 180 control unit
200 frame
201 speckle image sensor
202 object image sensor
203 optical filter
204, 205 actuator
210 frame
211 speckle image sensor
212 object image sensor
213 optical filter
214 optical system
215, 216 actuator
301 to 305, 311, 312 OCL
321 to 325 object pixel FD
331, 332 speckle pixel FD
341 to 345, 351, 352 read transistor
401 to 406 OCL
411 to 416 object pixel FD
421 to 423 speckle pixel FD
431 to 436, 441 to 443 read transistor

The invention claimed is:

1. An imaging apparatus, comprising:
a first optical system;
a first image sensor configured to:
image light that enters the first image sensor from an object, wherein the light is entered via the first optical system; and
generate image data of the object based on the imaged light;
a second image sensor configured to:
image a speckle pattern formed based on scatter of the light that strikes the object; and
generate image data of the speckle pattern, wherein
the speckle pattern enters the second image sensor via the first optical system, and
the first image sensor and the second image sensor are placed side by side in an optical axis direction of the first optical system; and
a second optical system between the first image sensor and the second image sensor, wherein the second optical system is movable in the optical axis direction of the first optical system.

2. The imaging apparatus according to claim 1, wherein the second image sensor is on a side opposite to the object, and
the first image sensor is between the object and the second image sensor in the optical axis direction of the first optical system.

3. The imaging apparatus according to claim 2, wherein the first image sensor is further configured to transmit a portion of the light that enters the first image sensor through the first optical system, and
the portion of the light is in a wavelength region receivable by the second image sensor.

4. The imaging apparatus according to claim 1, wherein the first image sensor and the second image sensor are electrically coupled by a bump.

5. The imaging apparatus according to claim 1, wherein the second optical system is a lens, and
the lens is configured to change at least one of a shape of the lens or a refractive index of the lens based on an external signal.

6. The imaging apparatus according to claim 1, wherein the first image sensor is further configured to:
receive visible light; and
generate the image data of the object based on the received visible light, and the second image sensor is further configured to:
receive infrared light; and
generate the image data of the speckle pattern based on the received infrared light.

7. The imaging apparatus according to claim 1, wherein a cell size of the second image sensor is greater than a cell size of the first image sensor.

8. The imaging apparatus according to claim 1, wherein a frame rate of the image data of the speckle pattern generated by the second image sensor is higher than a frame rate of the image data of the object generated by the first image sensor.

9. An imaging apparatus, comprising:
an optical system;
a first image sensor configured to:
image light that enters the first image sensor from an object, wherein the light is entered via the optical system; and
generate image data of the object based on the imaged light; and
a second image sensor configured to:
image a speckle pattern formed based on scatter of the light that strikes the object; and
generate image data of the speckle pattern, wherein
the speckle pattern enters the second image sensor via the optical system,
the first image sensor and the second image sensor are placed side by side in an optical axis direction of the optical system, and
at least one of the first image sensor or the second image sensor is further configured to move in the optical axis direction of the optical system.

10. An image sensor, comprising:
an optical system;
a first light reception unit configured to:
receive light that enters the first light reception unit from an object, wherein the light is entered via the optical system; and
generate image data of the object based on the received light;
a second light reception unit configured to:
receive a speckle pattern formed based on scatter of the light that strikes the object; and
generate image data of the speckle pattern, wherein
the speckle pattern enters the second light reception unit via the optical system, and
the first light reception unit and the second light reception unit are on a single substrate;
a first on-chip lens in the first light reception unit; and
a second on-chip lens in the second light reception unit, wherein the first on-chip lens and the second on-chip lens have different shapes.

11. The image sensor according to claim 10, wherein the second light reception unit is on a side opposite to the object, and
the first light reception unit is between the object and the second light reception unit in an optical axis direction of the optical system.

12. The image sensor according to claim 10, wherein the second light reception unit is longer than the first light reception unit in an optical axis direction of the optical system.

13. The image sensor according to claim 10, wherein a cell size of the second light reception unit is greater than a cell size of the first light reception unit.

14. The image sensor according to claim 10, wherein a frame rate of the image data of the speckle pattern generated by the second light reception unit is higher than a frame rate of the image data of the object generated by the first light reception unit.

* * * * *